(12) United States Patent
King

(10) Patent No.: US 7,305,115 B2
(45) Date of Patent: Dec. 4, 2007

(54) METHOD AND SYSTEM FOR IMPROVING ABILITY OF A MACHINE VISION SYSTEM TO DISCRIMINATE FEATURES OF A TARGET

(75) Inventor: Steven Joseph King, Merrimack, NH (US)

(73) Assignee: Siemens Energy and Automation, Inc., Iselin, NJ (US)

( * ) Notice: Subject to any disclaimer, the term of this patent is extended or adjusted under 35 U.S.C. 154(b) by 972 days.

(21) Appl. No.: 10/081,127

(22) Filed: Feb. 22, 2002

(65) Prior Publication Data
US 2003/0161524 A1    Aug. 28, 2003

(51) Int. Cl.
G06K 9/00 (2006.01)
G06F 19/00 (2006.01)
H04N 7/18 (2006.01)
H04N 9/47 (2006.01)

(52) U.S. Cl. .................... 382/141; 700/95; 348/86; 348/125

(58) Field of Classification Search ........ 382/141–147; 700/95–212; 29/833; 348/86–87, 92, 94–95, 348/125–128
See application file for complete search history.

(56) References Cited

U.S. PATENT DOCUMENTS

| | | | |
|---|---|---|---|
| 3,710,128 A * | 1/1973 | Kubisiak | 250/559.06 |
| 3,764,218 A * | 10/1973 | Schedewie | 250/550 |
| 4,806,776 A * | 2/1989 | Kley | 250/559.24 |
| 5,016,173 A * | 5/1991 | Kenet et al. | 382/165 |
| 5,448,453 A * | 9/1995 | Oshio | 362/510 |
| 5,463,697 A * | 10/1995 | Toda et al. | 382/199 |
| 5,717,518 A * | 2/1998 | Shafer et al. | 359/357 |
| 5,729,216 A * | 3/1998 | Sasaki et al. | 348/135 |
| 5,914,784 A * | 6/1999 | Ausschnitt et al. | 250/559.36 |
| 6,252,981 B1 * | 6/2001 | Guest et al. | 382/149 |
| 6,337,767 B1 * | 1/2002 | Takeuchi | 359/388 |

OTHER PUBLICATIONS

Murnaghan Instruments, 1999, "UV 35 Ultraviolet Passing—visible blocking CCD filter". (pp. 1-3).*
Schneider Optics, 1999, "Filter for motion pictures and television". (pp. 1-24).*
Archive.org, 2000, "Nerlite DOAL and COAL Illuminators" (here Nerlite) (pp. 1-3).*

* cited by examiner

Primary Examiner—Bhavesh M Mehta
Assistant Examiner—Manav Seth
(74) Attorney, Agent, or Firm—Bourque & Associates

(57) ABSTRACT

A method and system is disclosed to improve the ability of a machine vision system to distinguish desired features of a target by taking images of the target under different one or more lighting conditions and using image analysis to extract information of interest about the target. Ultraviolet light is used alone or in connection with direct on-axis and/or low angle lighting to highlight different features of the target. One or more filters disposed between the target and the camera help to filter out unwanted light from the one or more images taken by the camera. The images may be analyzed by conventional image analysis techniques and the results recorded or displayed on a computer display device.

13 Claims, 4 Drawing Sheets

METHOD AND SYSTEM FOR IMPROVING ABILITY OF A MACHINE VISION SYSTEM TO DISCRIMINATE FEATURES OF A TARGET

TECHNICAL FIELD

The present invention relates to machine vision systems and more particularly, to a system and method for locating small objects placed on a surface of an object such as integrated circuits.

BACKGROUND INFORMATION

Machine vision systems are used in numerous applications including, in particular, in electronics manufacture and assembly, such as inspection of electronic components, die alignment and inspection, package singulation inspection and lead inspection.

In one example, a video camera is placed at a fixed location with respect to one or more objects to be viewed. Knowing the location of the camera and the field of view of the camera optics, specific information can be obtained about the objects. The video information can be analyzed mathematically to obtain information that may be manipulated and stored.

In one example, integrated circuits are placed in a JEDEC tray for examination under a machine vision inspection system. It is of interest to discern the relative location of connection pads on the integrated circuit with respect to the edges of the integrated circuit packages. Thus, it is important to be able to discriminate the pads from the edges of the package.

In order to be able to discriminate the pads from the edges of the package, the reflected illumination off the pads should to be clearly distinguishable from the package edges and background. In many cases, the reflectance of the pads and edges are too similar to be able to clearly and automatically distinguish and differentiate the two. In other applications, the reflected light from the pads is so great as to cause bloom in the video camera and obscure the edges.

Where there is a sufficient difference in height between the background and objects, point illumination at an angle can help to make the object edges show up more clearly. However, often such height differences do not exist.

What is needed is a system and method that is able to reliably and clearly distinguish between objects in the field of view of the video camera.

SUMMARY

The present invention includes several novel features. The first novel feature is the use of Ultra Violet (UV) light (with proper filters) to image a device such as a Printed Circuit Board (PCB) substrate. The UV light causes the substrate to go bright while all metallic and black surfaces such as the part or holding tray remain dark. A Dual on axis light (DOAL) or similar light is used to illuminate the pads or other shiny surface of an object. The combination of the UV light to illuminate the part in one image, with a DOAL used to illuminate the pads or shiny surfaces on objects such as 'no-lead' devices in a second image provides a novel method by which various features of an object being inspected my be detected and their relative positions established and measured.

A second lighting combination is to use the UV light to illuminate and inspect on portion of the device, such as for the PCB, and then to use a RING light to illuminate solder balls, for example, on a Ball Grid Array (BGA) device. It is very common to process both small BGAs and 'no-lead' SIP packages on the same system, therefore a system and method in accordance with the present invention is very advantageous.

A second feature of the present invention is that sometimes the UV image, with the proper filtering, is enough to see the part edges as bright and the pad edges as dark. Thus both features are distinguishable in the same image. This means that there are times when the second image with the DOAL on 'no-lead' devices is unnecessary.

A machine vision method and system is described according to the principles of the present invention having a camera which may be connected to a computer, for processing of visual information about a target seen by the camera. The target may be illuminated sequentially by a conventional light source, an ultraviolet light source and a DOAL light source, with images collected under each lighting condition. The multiple images may be compared and combined to extract information about the target. The ultra-violet light source may be filtered to block visible light, and the camera's field of view may be filtered so as to block ultraviolet light.

BRIEF DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Figure 1:
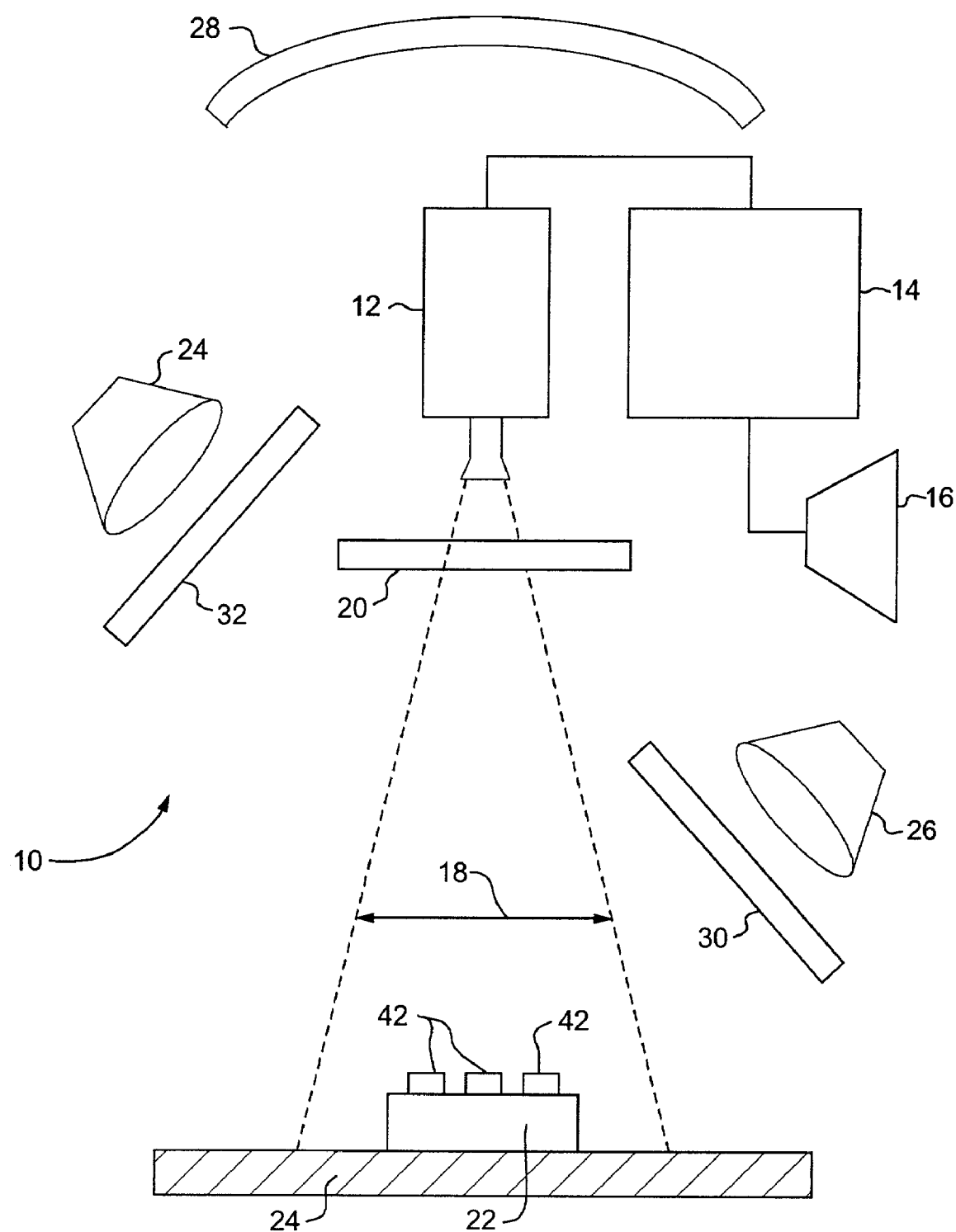
FIG. 1 is a schematic diagram of a machine vision system according to the principles of the present invention.

One embodiment 10 according to the principles of the present invention is shown in FIG. 1. A camera 12 is connected to a computer 14 and optionally a display device 16. In one implementation, the camera 12 is a video camera having a digital output signal. Other types of cameras are also suitable for different applications. An optional recording device (not shown) may also be used to keep a record of what is seen by the camera 12.

The field of view designated generally by the arrow 18 of the camera 12 may be optionally filtered by an optical filter 20. More than one optical filter 20 may be used to obtain views from the camera under different lighting conditions. Within the field of view 18 of the camera 12 is one or more targets 22 supported by a platform 24. The platform 24 may include a moving conveyor belt or an adjustable tray (not shown). The target 22 may contain one or more objects 42 each having details of interest.

The field of view 18 of the camera 12 may be illuminated by a variety of different light sources. In the embodiment shown, a conventional light source 24 such as a low angle diffuse light source possibly made up of multiple off axis LED's is shown, as well as a high angle ultraviolet light source 26 and a diffuse on-axis light (DOAL) source 28.

The ultraviolet light source 26 may be fitted with one or more filters 30. The ultraviolet light source 26 is shown with a filter 30 designed to block visible light. Other filters may also be used so as to allow illumination by a limited spectrum of ultraviolet light.

In operation, separate views of the target 22 with one or more objects of interest 42 are taken by camera 12 with the target 22 illuminated only by the conventional light source 24, only by the ultraviolet light source 26 and only by the DOAL light source 28, respectively. These views may be analyzed and combined/subtracted or otherwise processed to extract information about the target and its features of interest, and the results may optionally be shown on the display device 16 or stored for later retrieval. For example, the views may be superpositioned to extract information associated with the one or more objects.

Figure 2:
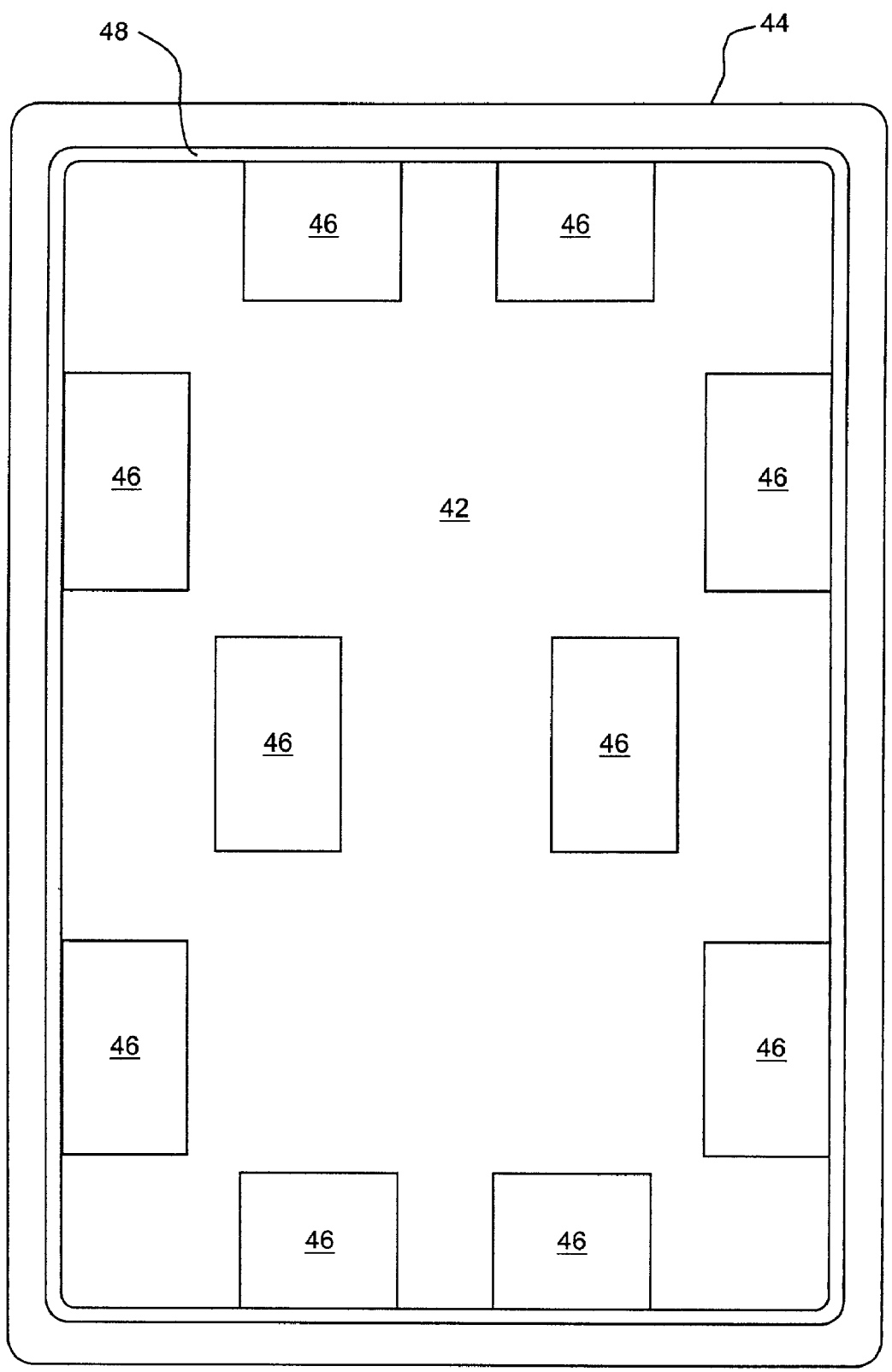
FIG. 2 is a photograph of a target integrated circuit using conventional lighting.

Referring to FIG. 2, a view is shown of an integrated circuit 42 held in a JEDEC tray 44 illuminated by a conventional light source 24. The integrated circuit 42 has one or more connection pads 46, and an edge 48. It is difficult to discern from this single view where pad 46 ends and edge 48 begins. The image of the edge 48 and the pad 46 are nearly indistinguishable.

Figure 3:
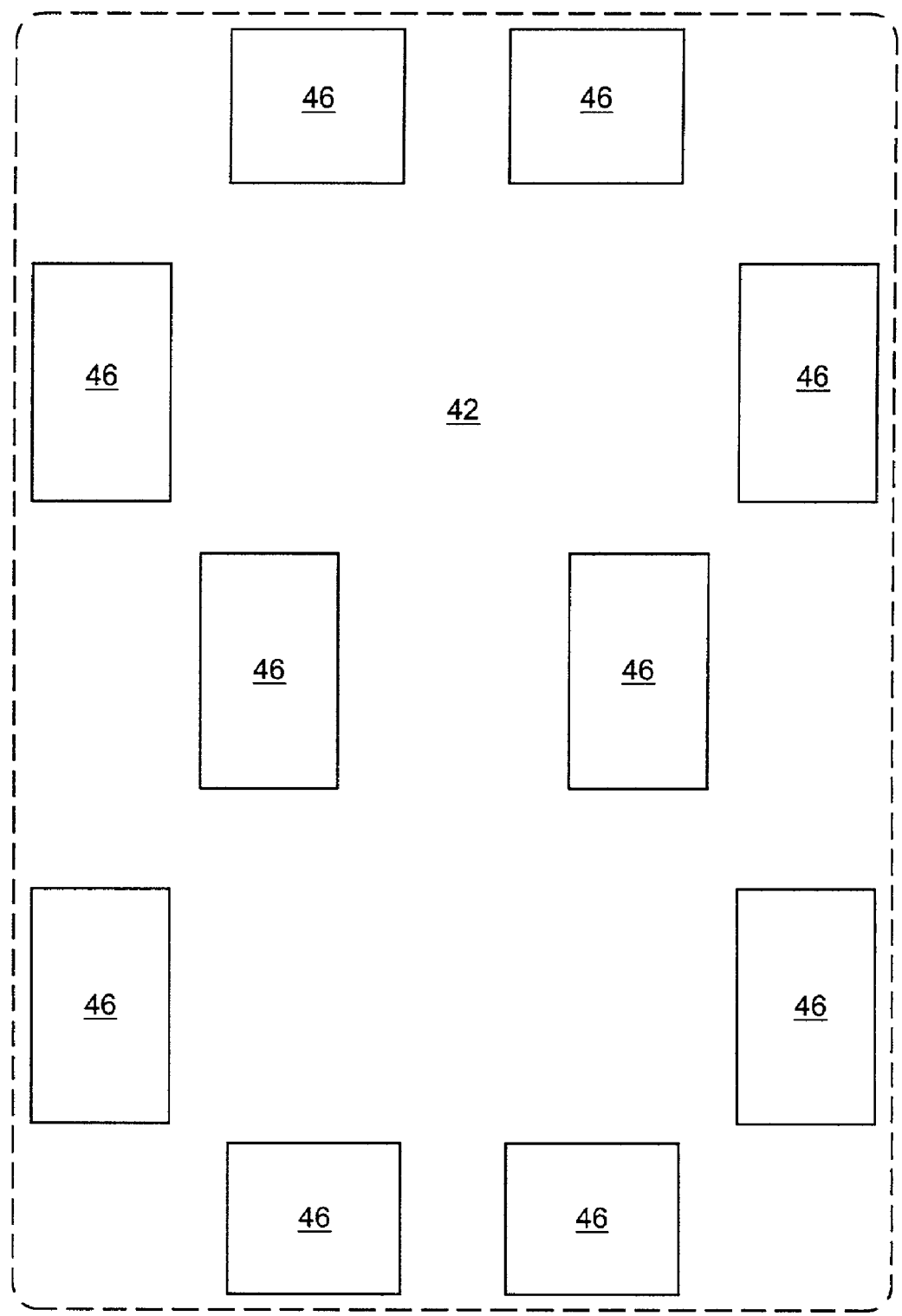
FIG. 3 is a photograph of the same target as in FIG. 2 lighted with an ultra-violet light source.

Referring to FIG. 3, a view of the same integrated circuit 42 is shown, this time illuminated only by the ultraviolet light source 26. In this embodiment, the pad 40 fluoresces in the visible region when illuminated by ultraviolet light, but the package (including the edge 48) of the integrated circuit 42 does not. Accordingly, the outlines of pad 46 are clearly discernable.

Figure 4:
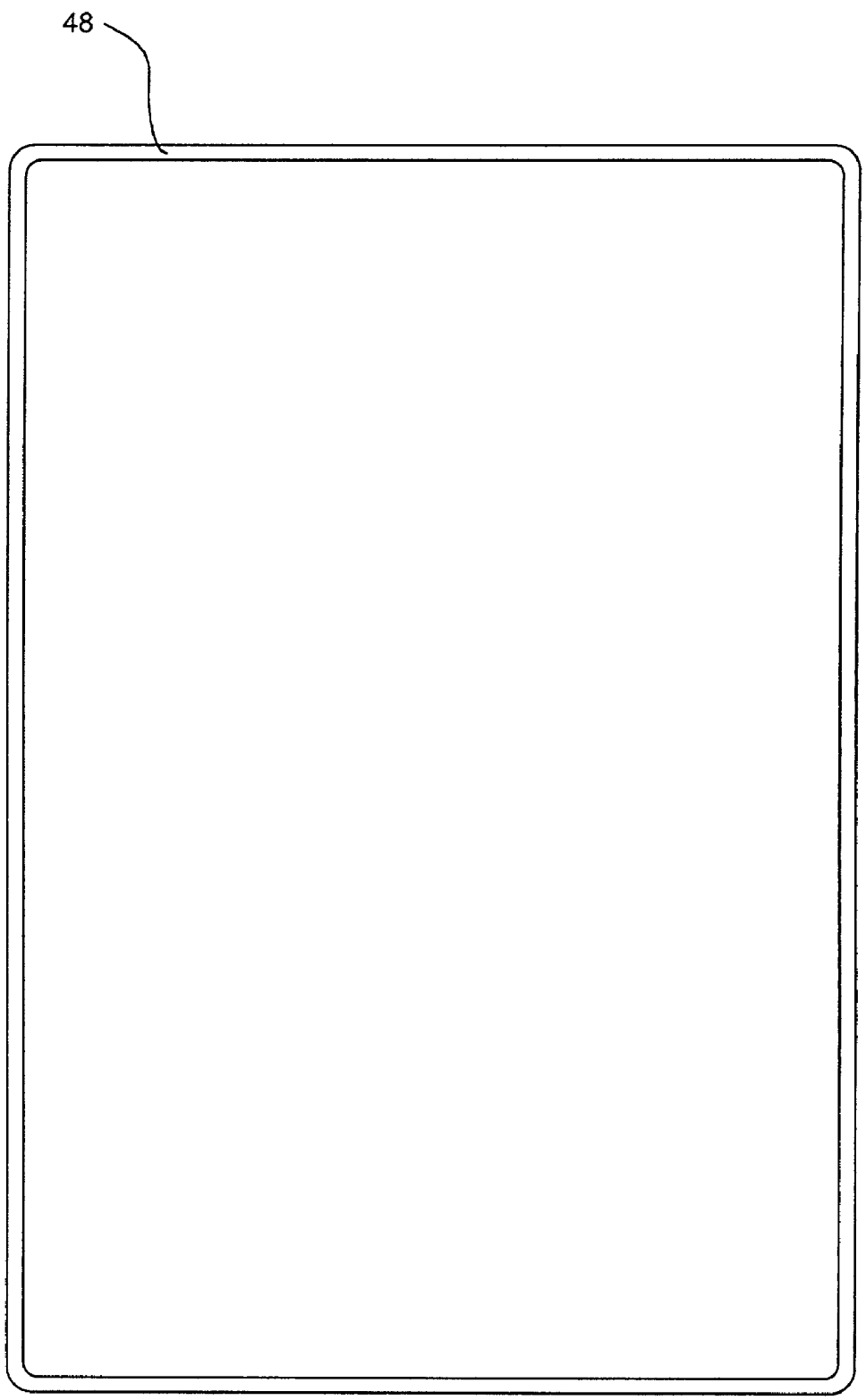
FIG. 4 is a photograph of the same target lighted with a diffuse on-axis light source.

Referring now to FIG. 4, the same integrated circuit 42 is shown illuminated by a DOAL light source. While the pad 40 is no longer clearly distinguishable from the edge 48, the outer perimeter of the integrated circuit 42 (including edge 48) may clearly be seen.

By combining the information in the views shown in FIGS. 3 and 4, the location of the pad 40 may be determined relative to the edge 48. As may be seen, other information about other features of the target integrated circuit 42 may be extracted using known image processing techniques applied to each image alone and in combination.

In the embodiment shown, a filter 30 is used on the ultraviolet light source 26 to block light with wavelengths greater than 390 nanometers. Other wavelengths of light may be used beneficially, depending upon the characteristics of the target. A filter may also be used having one or more bandpass regions. Similarly, in the embodiment described, the field of view 18 of the camera 12 has a filter which passes light with wavelengths greater than 410 nanometers. Other wavelengths of light may be chosen, as well as using filters having one or more bandpass regions. The choice of lighting will depend upon the characteristics of the target, and should be chosen so as to maximally distinguish desirable elements of the target under different lighting conditions.

Modifications and substitutions by one of ordinary skill in the art are considered to be within the scope of the present invention, which is not to be limited except by the following claims. For example, views may be used and compared using different spectra of visible light, or visible light regions combined with ultraviolet light. The angle of illumination of the infrared light and conventional light sources may be varied so as to maximize the ability to discriminate desirable features of the target.

What is claimed is:

1. A system comprising
   a camera;
   a first visible spectrum illumination source;
   at least a second ultraviolet spectrum illumination source; and
   a computer, connected to the camera, to receive an image from the camera, wherein the camera is capable of taking a first image of a target illuminated by at least the first illumination source, and further capable of taking a second image of the target illuminated by at least the second illumination source and wherein the first and second images are able to be analyzed in the computer to determine an edge of at least a portion of the target.

2. The system of claim 1 wherein the camera comprises a video camera.

3. The system of claim 1 wherein the analysis by the computer comprises superposition of the first image and the second image.

4. The system of claim 1 wherein the first illumination source comprises a diffuse on axis light source.

5. The system of claim 1 further comprising at least one filter disposed between the target and the second illumination source, which filter blocks visible light.

6. The system of claim 5 wherein the filter blocks wavelengths of light greater than 390 nanometers.

7. The system of claim 1 further comprising at least one filter disposed between the camera and the target.

8. The system of claim 7 wherein the filter blocks ultraviolet light.

9. The system of claim 8 wherein the filter blocks light with a wavelength shorter than 410 nanometers.

10. The system of claim 9 wherein the filter blocks at least one portion of the visible spectrum.

11. A method comprising:
    providing a camera connected to a computer having storage, an input to receive at least first and second images and an output providing extracted image information;
    providing a filter disposed between the camera and the target, which filter blocks ultraviolet light;
    using the camera to obtain a first image of the target and sending the image to the computer while the target is illuminated by a first visible spectrum illumination source comprising a diffuse on-axis light;
    using the camera to obtain a second image of the target and sending the image to the computer while the target is illuminated by at least a second illumination source comprising an ultraviolet light; and
    using the computer to analyze the first and second image to extract information about the target to determine an edge of at least a portion of the target.

12. A method comprising:
    providing a camera connected to a computer having storage, an input to receive at least a first image, a second image, and an output providing extracted image information;
    providing a visible light filter disposed between the camera and the target, which visible light filter blocks visible light;
    providing an ultraviolet light filter disposed between the camera and the target, which ultraviolet light filter blocks ultraviolet light;
    using the camera to obtain a first image of the target and sending the image to the computer while the target is illuminated by a first illumination source comprising an ultra-violet light and the visible light filter is provided;
    using the camera to obtain a second image of the target and sending the image to the computer while the target is illuminated by said first illumination source and the ultraviolet light filter is provided; and using the computer to analyze the first image and the second image to extract edge information about the target.

13. A system comprising a camera;

a first target illumination source comprising a visible light source;

a second target illumination source comprising an ultraviolet light source;

a filter disposed between the camera and said target; and a computer, connected to the camera, to receive an image from the camera, wherein the camera is capable of taking at least first image of said target illuminated by said ultraviolet light source and second image of said target illuminated by said visible light source, and wherein the first image and second image are able to be analyzed in the computer to extract dimensional information about the target.

* * * * *